United States Patent [19]

Kirchhoff et al.

[11] Patent Number: 5,431,800
[45] Date of Patent: Jul. 11, 1995

[54] LAYERED ELECTRODES WITH INORGANIC THIN FILMS AND METHOD FOR PRODUCING THE SAME

[75] Inventors: Jon R. Kirchhoff; Dean M. Giolando, both of Toledo, Ohio

[73] Assignee: The University of Toledo, Toledo, Ohio

[21] Appl. No.: 147,573

[22] Filed: Nov. 5, 1993

[51] Int. Cl.6 ............ G01N 27/26; C25B 11/00; B05D 5/12; C23C 16/00
[52] U.S. Cl. .................. 204/290 R; 204/294; 204/403; 204/419; 427/99; 427/249; 427/255.3
[58] Field of Search .......... 204/403, 415, 419, 421, 204/290 R, 294; 427/99, 249, 255.3

[56] References Cited

U.S. PATENT DOCUMENTS

| | | | |
|---|---|---|---|
| 3,808,035 | 4/1974 | Skelter | 117/106 R |
| 4,212,663 | 7/1980 | Aslami | 65/144 |
| 4,261,722 | 4/1981 | Novak et al. | 65/60 D |
| 4,312,734 | 1/1982 | Nichols | 204/419 |
| 4,528,085 | 7/1985 | Kitajima et al. | 204/419 |
| 4,705,646 | 11/1987 | DuPont et al. | 252/511 |
| 4,721,601 | 1/1988 | Wrighton et al. | 422/68 |
| 4,810,526 | 3/1989 | Ito et al. | 427/249 |
| 4,959,130 | 8/1990 | Josowicz et al. | 204/32.1 |
| 4,998,159 | 3/1991 | Shinohara et al. | 357/80 |
| 5,037,525 | 8/1991 | Badwal | 204/421 |
| 5,086,351 | 2/1992 | Couput et al. | 359/265 |
| 5,090,985 | 2/1992 | Soubeyrand et al. | 65/60.52 |
| 5,158,083 | 10/1992 | Sacristan et al. | 128/635 |
| 5,169,508 | 12/1992 | Suzuki et al. | 204/290 R |
| 5,192,415 | 3/1993 | Yoshioka et al. | 204/403 |
| 5,204,314 | 4/1993 | Kirlin et al. | 427/255.3 |
| 5,246,881 | 8/1993 | Sandhu et al. | 427/99 |

*Primary Examiner*—John Niebling
*Assistant Examiner*—Bruce F. Bell
*Attorney, Agent, or Firm*—Marshall & Melhorn

[57] ABSTRACT

A method for the preparation of layered electrodes, including ultramicroelectrodes, through application of a thin film coating of an inorganic material to a conductor by use of chemical vapor deposition. The chemical vapor deposition techniques of the present invention provide a layered electrode that is efficiently and effectively manufactured in a standard reaction chamber at atmospheric pressure. The preferred conductors are carbon fibers and foams, and metal (platinum or gold) wires, meshes and foams. The precursors for the thin film deposition include those that yield thin-films of insulators, semiconductors, metals, and superconductors. During the chemical vapor deposition process, a thin film coating is formed on the conductor by the pyrolytic decomposition of the precursor vapor at the surface of the heated conductor. The hardness and rigidity of the thin film layer imparts durability and structure to the fragile and flexible conductors without significantly increasing the size of the device. The variable parameters in the deposition process are monitored and controlled so that the desired thickness of thin film coating will be obtained.

48 Claims, 4 Drawing Sheets

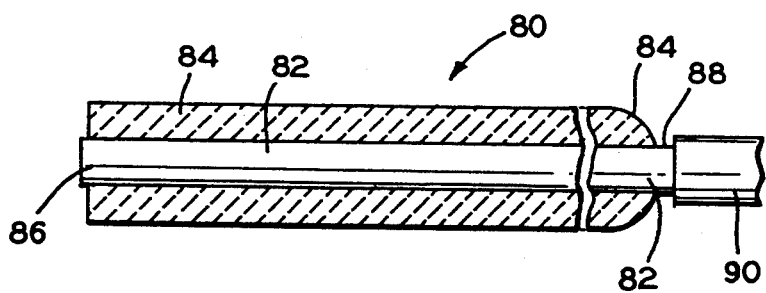
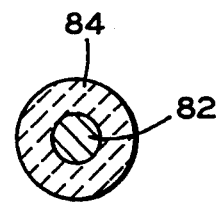
FIG. 3        FIG. 4
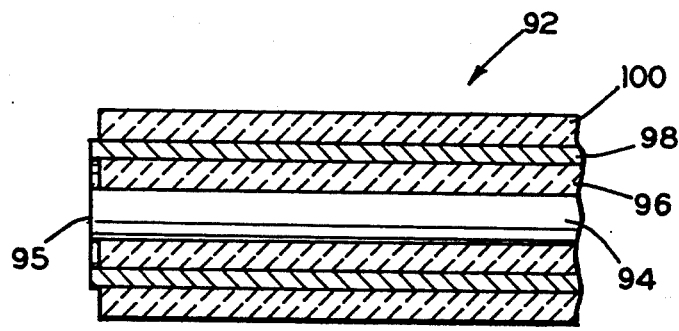
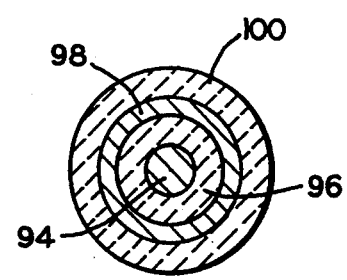
FIG. 5        FIG. 5A
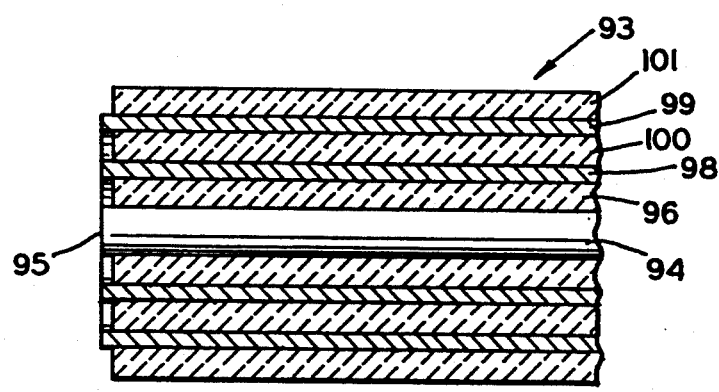
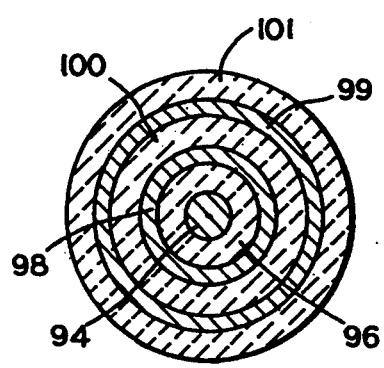
FIG. 6        FIG. 6A

LAYERED ELECTRODES WITH INORGANIC THIN FILMS AND METHOD FOR PRODUCING THE SAME

BACKGROUND OF THE INVENTION

1. Field of the Invention

The present invention relates to layered electrodes, and more particularly, to ultramicroelectrodes and various layered electrodes with thin film inorganic coatings. Chemical vapor deposition is used to apply an inorganic thin film coating to carbon fibers and foams, and metal wires, meshes and foams. The ultramicroelectrodes have highly reproducible electrode dimensions with improved sensitivity and electrochemical response.

2. Summary of Related Art

Electrodes are used for carrying or emitting electric charges (or electric charge carriers) and are often manufactured in a layered configuration. Layered electrodes are used in a wide variety of applications and in a number of different configurations. The chemical vapor deposition process for depositing thin layers of inorganic films provide a means for depositing insulating, semiconductor, metal, or superconductor film layers on extremely small conductors.

One of the primary applications for the present invention is for ultramicroelectrodes used in biosystems, microenvironments, gas phase detection, and ion-selective systems. Ultramicroelectrodes are made from very thin electric conductors with thicknesses (tip diameters) in the range of 0.5 to 50 micrometers. The ultramicroelectrodes are made from carbon fibers or metal wire of less than 10 micrometers. With the deposition of multiple layers of inorganic thin films in the present invention, the ultramicroelectrode provides an electrode with the desired structural integrity, performance characteristics and an overall diameter of less than 50 micrometers.

The majority of ultramicroelectrodes in use at this time are encased in a glass capillary. An insulating layer of glass with an epoxy resin seal is formed on the conductors to provide rigidity and structure to the conductors. Certain polymers have also been used to insulate the conductors of an ultramicroelectrode.

However, the use of the glass capillary system significantly increases the size of the ultramicroelectrode and results in a very fragile device. The size of the glass capillary (diameters of over 2 millimeters) makes the electrode too large for many applications.

Hairline fractures may occur in the glass because of the thermal stress caused by the difference of the thermal expansion coefficient in the glass and the conductor material. The cracks cause a changing surface area for obtaining electrode readings, which effects the reliability of the device.

The poor adhesion of the coating material to the conductor permits fluid to accumulate under the insulation. In addition, epoxy resins have poor stability with respect to organic solvents, which leads to the degradation of the epoxy insulation. These two problems could obviously effect the accuracy and reliability of the ultramicroelectrode in electrode measurements.

Because of the performance problems with glass and epoxy insulation, an increase in the residual current takes place. The signal/noise ratio is often unacceptable and the response time and reproducibility of the results are adversely affected. Many ultramicroelectrodes are still made by hand, which results in inefficient production operations, poor reproducibility, and non-competitive product costs.

Ultramicroelectrodes are used in applications based on both potentiometric and voltametric measurements. In general, only the tip of the ultramicroelectrode is exposed to the analyte solution. As the dimensions of the tip decrease, the quality of the voltammetric information increase and the ability to perform measurements in extremely small microenvironments or sub-microliter sample volumes is possible.

A major impetus for the development of voltammetric ultramicroelectrodes has been for in vivo measurements of electroactive species in biological microenvironments. Microelectrodes with diameters of 10 micrometers were used for electroanalytical probes of brain neurotransmitters. More recent efforts have focused on the development of ultramicroelectrode probes for measurements in single-cells with minimal perturbation of the cellular environment, which permits the investigation of chemical profiles at the cellular level. An improved ultramicroelectrode would benefit studies in biochemistry, cell biology, pharmacology, pharmacokinetics, and toxicology.

Ultramicroelectrodes will find widespread applications in electrochemical detection methods, including components of in vivo biosensors. Electrochemical methods are routinely used for analysis in a variety of clinical settings. Ultramicroelectrodes are being used in such processes as chromatography and capillary electrophoresis. Ultramicroelectrodes may also be used in such areas as neonatal units, where analysis can be performed without the need to continually draw blood samples from a premature baby with a limited blood supply.

Ultramicroelectrodes are also valuable for the investigation of interfacial phenomena within the diffusion layer of conventional electrodes. Since the diffusion layer typically extends less than a few hundred micrometers from the electrode surface, the small dimension of ultramicroelectrodes are well suited to achieve the spatial and temporal resolution necessary to observe changes in interfacial concentrations of the products and reactants of electrochemical reactions at larger electrodes.

Scanning electrochemical microscopy uses the small tip diameter of the ultramicroelectrodes to probe the character and reactivity of electrode surfaces with lateral resolution approaching the 100 Angstrom level.

As the microenvironment for analysis moves into cellular dimensions, or dimensions less than the thickness of the diffusion layer, one of the most important considerations is simply the physical size of the ultramicroelectrode probe. Carbon fiber or metal wire disk electrodes are constructed from fibers or wires with a diameter of 0.5 to 10 micrometers. If the insulation layer can be kept at a minimum thickness through the deposition of a thin film of an inorganic insulation layer, without compromising the performance of the ultramicroelectrode, improved measurements will be available from ultramicro-environments.

Electrodes fabricated by chemical vapor deposition techniques of inorganic thin films may be used in a number of other applications in addition to the ultramicroelectrodes for biosensors and other electrochemical detection applications. Metal mesh electrode applications include the use of thin meshes with thickness in the same micrometer range (less than 50 micrometers) deposited with one or more layers of inorganic thin film.

The metal mesh electrodes may be used as modified optical transparent electrodes, photo conducting arrays, acoustic conducting arrays, and conductor electrode arrays for such application as electrochromic display devices or solar cell collectors. In such electrochromic or solar cell devices, the inorganic thin film coating is a semiconductive, metallic, or superconductive thin film coating to enhance the charge carrying and/or charge storage capabilities of the mesh electrode.

Other applications utilizing electrodes made from the chemical vapor deposition process of the present invention include thin film coating of carbon foams and metal foams for use in electrocatalytic devices and flow through detectors. The electrodes may also be used for battery and photocell applications by combining, for example a plate conductor with an adjacent electroconductive ceramic plate.

The substrate materials and the layers of inorganic thin films may be selected from a variety of materials and may be applied in a number of different configurations. The inorganic thin film coating may be an insulating, semiconductive, metallic, or photosensitive material. In a number of different industries, there is a need for improved electrodes and smaller electrodes that are easy and cost effective to manufacture, and that provide the desired performance characteristics based on the materials and configuration of the electrode.

An ultramicroelectrode is disclosed in U.S. Pat. No. 4,959,130 (Josowicz et al.) utilizing a wire or filament of a noble metal or carbon on which polymer insulating layer is formed. The insulating layer is made from a compound consisting of substituted poly(1,4-phenylene) ethers, poly(1,4-phenylene) thioethers and poly(1,4-anilines), whose plurality of phenyl groups are cross-linked at their ortho-positions by alkylene groups with from two to ten carbon atoms.

U.S. Pat. No. 5,158,083 to Sacristan et al. discloses a miniature $pCO_2$ probe. The probe includes a miniaturized glass bulb pH sensor arranged in a flexible hollow tube.

A dry glass electrode for use in potentiometric analyses of aqueous media is shown in U.S. Pat. No. 4,312,734 (Nichols). The conductor element is covered by an ion-selective glass, and the conductor element and the glass are heated to provide a seal and then cooled to anneal the glass.

U.S. Pat. No. 5,192,415 to Yoshioka et al. discloses a biosensor utilizing an electrode system made from conductive carbon paste.

U.S. Pat. No. 5,086,351 to Couput et al. shows an electrochromic element having an electrolyte ion conducting layer interposed between first and second inorganic electrochromic layers.

Chemical vapor deposition is known in a number of industries, and such a process has been used to deposit thin film coatings on glass and other substrates.

U.S. Pat. No. 3,808,035 to Stelter discloses a chemical vapor system for deposition of a single or multiple layers from a dilute gas sweep onto a variety of substrates.

A method for applying an inorganic coating to a glass surface was shown in U.S. Pat. No. 4,261,722 (Novak et al.). A gas stream containing a vapor of a metal compound which is thermally decomposable is directed onto a surface at an elevated temperature. The relative humidity is controlled to increase the rate of formation of the metal oxide on the surface.

U.S. Pat. No. 5,090,985 to Soubeyrand et al. discloses a method for preparing vaporized reactants consisting of a coating precursor and a blend gas for chemical vapor deposition.

It must be noted that the prior art referred to hereinabove has been collected and examined only in light of the present invention as a guide. It is not to be inferred that such diverse art would otherwise be assembled absent the motivation provided by the present invention.

It would be desirable to be able to provide a low cost electrode, including an ultramicroelectrode and a metal mesh electrode, that is reproducible from both a dimensional and performance standpoint. Another desirable feature would be to provide a quality seal between the conductor and the insulator without epoxy or other sealant. In the biosensor applications, it would also be desirable to provide a ceramic insulation which is inert and biocompatible.

SUMMARY OF THE INVENTION

In accordance with the present invention, there is provided a method for the preparation of electrodes, including ultramicroelectrodes, through application of a thin film coating of an inorganic material to a conductor by use of chemical vapor deposition. The chemical vapor deposition techniques of the present invention provide an electrode that is efficiently and effectively manufactured in a standard reaction chamber at atmospheric pressure.

The composition and configuration of the conductor and the thin film coating for the electrode can be selected to meet the specific application requirements for the electrode. The preferred conductors are carbon fibers and foams, and metal (platinum or gold) wires, meshes and foams. Thin film formation on these conductors which will produce a variety of devices with varying utility. The precursors are sources for thin films of insulative, semiconductive, metallic, and superconductive materials.

During the chemical vapor deposition process, the conductors for the electrodes are mounted on a holder and positioned in the reaction chamber. The conductors are connected to a power supply for resistive heating of the conductors. The mixture of a precursor vapor and blend gas are conveyed from the vaporization chamber to the reaction chamber. The mixture of precursor vapor and blend gas are directed over the conductors in the reaction chamber such that an inorganic thin film coating is formed on the conductor by the pyrolytic decomposition of the precursor vapor at the surface of the heated conductor.

For ultramicroelectrodes formed from conductors of carbon fibers or metal wires, the structural characteristics of the thin film layer impart durability and structure to the fragile conductors without significantly increasing the size of the device. The inorganic thin film may result in a rigid electrode or in a flexible electrode with a specified elasticity, based on the inorganic thin film coating process.

The variable parameters in the deposition process are monitored and controlled so that the desired thickness of thin film will be obtained. The coated conductor is removed from the reaction chamber and trimmed to the desired length and/or configuration. Miniature leads are attached to the conductor so that the electrical state of the conductor can be monitored.

An object of the present invention is to build an ultramicroelectrode with overall dimension of 50 micrometers or less. For analysis in the cellular or diffusion layer dimensions, the ultramicroelectrode should be as small as possible without detriment to performance characteristics.

A further object of the invention is to produce an ultramicroelectrode with reproducible electrode dimensions. The present invention can produce electrodes in the desired micrometer range with dimension tolerance of approximately one micrometer, which provides a size reduction advantage and standardization advantage over the current microelectrodes.

An additional object of the present invention is to provide a uniform insulating (or conducting) coating about the conductor to provide a more accurate and reproducible electrode response.

An object of the present invention is to provide an improved seal between the conductor and the outer insulating coating without the use of epoxy or other sealants. The improve seal will provide longer electrode life and more accurate response.

A further object of the present invention is to enhance the electron transfer properties of the electrode. This enhancement provides increase sensitivity in the electrode.

An object of the present invention is to provide a process for manufacturing a variety of electrodes, including ultramicroelectrodes, that is simple to use and control from a production standpoint, and that is cost competitive and reproducible from a quality control concern. Electrodes can be prepared with a wide range of coatings simply by changing the precursor material. The thickness of the thin film deposition and the resulting size of the ultramicroelectrode can be varied by controlling the deposition time and the precursor flow rate. The equipment used for the chemical vapor deposition process is inexpensive and simple to operate.

BRIEF DESCRIPTION OF THE DRAWINGS

The above, as well as other advantages of the present invention, will become readily apparent to those skilled in the art from the following detailed description of a preferred embodiment when considered in the light of the accompanying drawings in which:

FIG. 3 is a longitudinal cross sectional view of an ultramicroelectrode provided with a single carbon fiber;

FIG. 4 is a cross sectional end view of the ultramicroelectrode of FIG. 3;

FIG. 5 is a longitudinal cross sectional view of an ultramicroelectrode provided with a center carbon fiber, a first insulating layer, a ring conductor, and a second insulating layer;

FIG. 5A is a cross sectional end view of the ultramicroelectrode in FIG. 5;

FIG. 6 is a longitudinal cross sectional view of an ultramicroelectrode provided with double ring construction, including a center carbon fiber, a first insulating layer, two ring conductors, and two additional insulating layers;

FIG. 6A is a cross sectional end view of the ultramicroelectrode in FIG. 6;

Corresponding reference numbers indicate corresponding parts throughout the several views of the drawings.

DESCRIPTION OF THE PREFERRED EMBODIMENT

Figure 1:
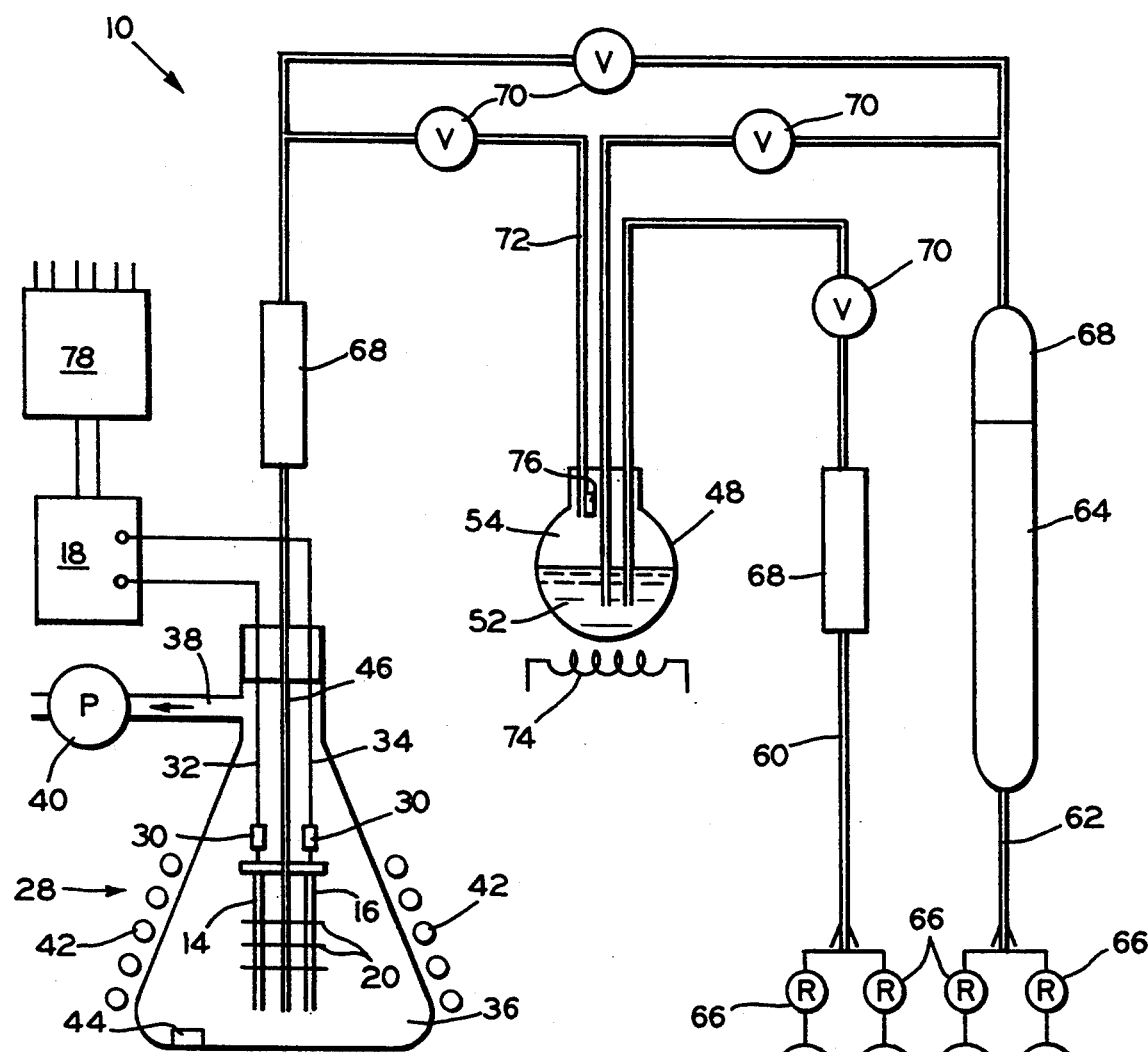
FIG. 1 is a schematic illustration of the apparatus for practicing the method of the present invention, and specifically the chemical vapor deposition process.
Figure 2:
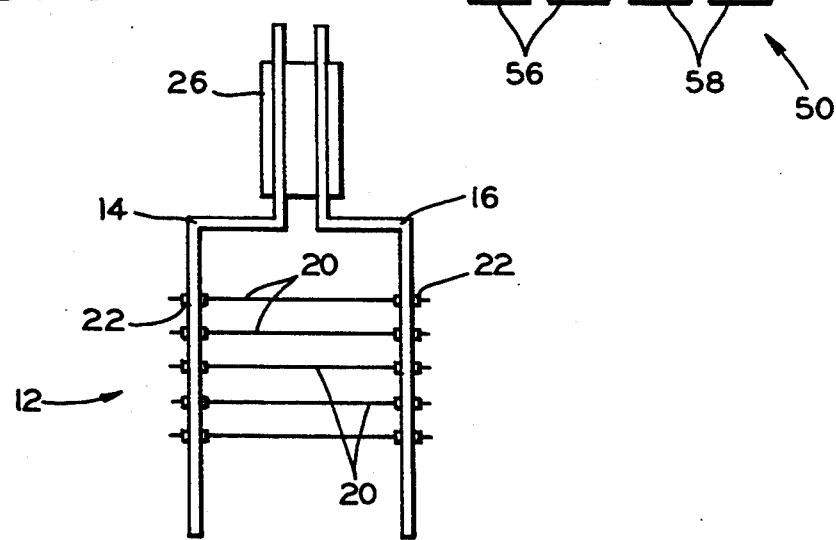
FIG. 2 illustrates an assembly of lengths of carbon fibers carried by an electrode holder and ready for placement in the reaction chamber as shown in FIG. 1.

The process for making electrodes and ultramicroelectrodes includes the chemical vapor deposition of a thin film coating on a conductor utilizing a system 10 as shown in FIGS. 1 and 2. One of the main components of the chemical vapor deposition system 10 is the electrode holder 12 for mounting the conductors 20 of the electrode and ultramicroelectrode.

The electrode holder 12 includes a pair of electrical leads 14, 16, typically made of copper, connected to the power supply 18 for conducting power to the conductors 20 for resistive heating of the conductors 20. The spacing between the electrical leads 14, 16 can be adjusted to accommodate the mounting of the conductors 20.

The electrical leads 14, 16 are provided with a number of electrical terminals 22 mounted opposite each other on the electrical leads 14, 16 for securing and supplying power to the conductors 20. If the terminals 22 are not acceptable to secure the conductors 20, a drop or two of silver epoxy can be used to secure the conductors 20 to the electrical leads 14, 16.

The power supply 18 is operable from a 115 volt power supply and supplies both AC and DC (variable voltage) power to the conductors 20 mounted between the electrical leads 14, 16. The resistive heating characteristics of most conductors 20 can be determined and the most efficient voltage for reaching the necessary conductor surface temperatures for chemical vapor deposition can be obtained from a relatively standard power supply 18.

A spacer 26 is used to maintain the proper spacing between the electrical leads 14, 16, and to facilitate the mounting of the electrode holder 12 in the reaction chamber 28. The spacer 26 is made from glass or other acceptable material.

The configuration of the electrode holder 12 can be changed to accommodate a conductor 20 made from mesh or foam substrates. The main requirement of the electrode holder 12 is to establish the necessary electrical connections for the resistive heating process.

The electrode holder 12 is suspended in the reaction chamber 28 by electrical clamps 30, which are connected to the electrical leads 14, 16. The clamps 30 are in electrical communication with the power supply 18 through support leads 32, 34.

The reaction chamber 28 is an enclosure with a precursor vapor discharge adjacent to the electrode holder 12 at one end 36 of the chamber 28, and an exhaust port 38 at the opposite end. In addition to the resistive heating of the conductors 20, the reaction chamber 28 includes a vacuum pump 40 to control the pressure in the reaction chamber 28. A temperature-pressure sensor 44 is mounted in the chamber 28.

In a reaction chamber 28 with a cold wall implementation of the chemical vapor deposition techniques, the chemical vapor deposition is an endothermic reaction such that the chemical reaction takes place on the surface of the conductor 20 where the temperature is the highest. In addition to the resistive heating method discussed above, induction heating is another known method for heating the conductors 20 in the reaction chamber 28. In the present system, a high frequency induction coil 42 can also be positioned about the chamber 28 and used with an insulated holder 12 to heat the conductors 20.

The precursor vapor used to create the thin film on the conductors 20 of the electrode is introduced into the reaction chamber 28 through supply tube 46. The precursor vapor delivered through the supply tube 46 contacts the conductor 20 in the reaction chamber 28 such that a thin film coating is formed on the conductor 20 by the pyrolytic decomposition of the precursor vapor at the surface of the heated conductor 20.

The precursor system for supplying the precursor vapor to the reaction chamber 28 includes a vaporization chamber 48. The precursor may initially be provided in a solid, liquid, or vapor form. A liquid precursor with a blend gas supply 50 is one of the most efficient means for supplying the precursor vapor. A liquid precursor 52 is placed in the vaporization chamber 48. The vaporization chamber 48 includes a vapor zone 54 in addition to the liquid precursor 52. One or more blend gases are bubbled through the liquid precursor 52 to mix the precursor with the blend gas and create a mixture of precursor vapor and blend gas for transmission to the reaction chamber 28. The precursor vapor reacts with the heated conductor 20 to create the desired coating at the surface of the heated conductor 20.

Possible blend gases include helium, nitrogen, hydrogen, argon, oxygen, and any other carrier gas which is chemically inert with the coating precursor 52. One or more of the blend gases are stored under pressure in cylinders 56 and 58. Some precursors require an oxygen blend, such as a thin film layer of silicon dioxide. Other precursors cannot be used with oxygen because of potential fire hazards.

The supply line 60 connected to cylinders 56 is for supplying oxygen as a blend gas. One or both of the cylinders 56 will be oxygen. The other supply line 62 includes a scrubbing system 64 to remove oxygen and water vapor from the blend gases supplied from cylinders 58. Hydrogen and argon are two of the preferred blend gases for cylinders 58.

The blend gas is pumped through regulators 66, flow meters 68, and valves 70 into the vaporization chamber 48. The precursor vapor and blend gas are discharged from the chamber 48 through supply line 72 through an additional flow meter 68 and valve 70 into the reaction chamber 28. The precursor in the vaporization chamber 48 may be heated using heater 74 to support the vaporization of the precursor. The temperature and pressure in the chamber 48 is monitored by sensor 76.

In addition to the liquid precursor system described above, the same system could be used to supply a precursor vapor from a vapor supply or a solid supply. The vapor precursor would be contained in a cylinder 58 and the vapor would pass through the system as noted above. The solid precursor would be positioned in chamber 48 and heated to a vapor state. In order to create the pressure differential between the reaction chamber 28 and the precursor chamber 48, the vacuum pump 40 could be used to reduce the pressure in the reaction chamber 28 and draw the vapor into the chamber 28 at the desired rate.

A controller 78 may be programmed for a variety of conductors, precursors, and blend gases. The controller 78 has an internal timing system and receives temperature and pressure signals from sensors 44, 76. The flow meters are also inputted into the controller 78. Output signals are generated to operate the regulators 66 and the valves 70 which control the concentration of the precursor vapor introduced into the reaction chamber 28. The controller 78 also controls the voltage supplied to the electrode holder 12 for resistive heating of the conductors 20. The controller 78 controls the deposition process such that the necessary vapor is supplied to the reaction chamber 28 and that the conductors 20 are at the proper temperature to ensure the desired reaction and resultant thin film coating on the conductors 20.

Because the conductors are typically very thin and because the film being deposited is very thin, the high concentration of precursor is not required. The vacuum pump 40 is not typically required. The process time is also relatively short. The components in the chemical vapor deposition are all fairly standard components which are low cost and easy to operate.

Referring now to FIGS. 3-9, several different embodiments of the ultramicroelectrodes and mesh-foam type electrodes are shown. The ultramicroelectrodes have an approximate thickness or diameter between 1.0 to 80 micrometers, with the typical thickness for traditional ultramicroelectrode applications being less than 50 micrometers. The conductor will have a thickness of 0.5 to 50.0 micrometers. The thin film layer is typically thinner (0.5 to 30.0 micrometers) than the thickness of the conductor with a somewhat inverse relationship. The very thin conductors often require a thicker film layer to provide rigidity and structural support. The conductors at the high end of the range can often function with a thinner layer of film.

FIGS. 3 and 4 show an ultramicroelectrode 80 with a single fiber 82 for the conductor and a thin film layer of material 84 formed on the fiber 82. The fibers would be mounted on the holder 12 as noted above and the layer 84 is deposited using the chemical vapor deposition process.

The fiber 82 is typically a carbon fiber, but could also be made from metal wire of platinum, gold, or other metal which can be formed in the desired diameter range. The fibers 82 have an approximate diameter of 10 micrometers, but can be smaller or larger depending on the application.

The thin film layer 84 is a film formed by chemical vapor deposition utilizing a ceramic coating precursor. The preferred refractory ceramics for this application include silicon carbide, titanium carbide, titanium boride, vanadium carbide, niobium nitride, aluminum nitride, and barium nitride. Other inorganic thin films may be used depending on the application to provide the desired electrical characteristics and rigidity to the fiber 82. Other examples of thin film inorganic layers which may be deposited include superconductors; metals such as gold, silver, and platinum; semiconductors such as tin oxide and indium oxide; and insulators such as silicon oxide and aluminum oxide.

Only the tip 86 of the conductor fiber 82 is exposed to an analyte solution. The opposite end 88 of the conductor fiber 82 is connected to a miniature lead 90 for conducting a signal from the electrode 80 to a monitoring device or other instrumentation (not shown).

The tip 86 and opposite end 88 are not covered and protected by any thin film insulation 84. The ultramicroelectrodes 80 is typically cut to length from the coated conductor 20, and the cutting action provides the exposed ends 82, 86. When larger conductors 20 are used, the film free regions may be masked before the chemical vapor deposition takes place or the thin film insulation 84 may be etched away after the initial deposition. Depending on the length of the electrode 80, several electrodes 80 could be formed from a conductor 20 in the electrode holder 12.

A major application for the voltammetric ultramicroelectrodes is in vivo measurements of electroactive species in biological microenvironments. The ultramicroelectrode 80 is also suitable for investigating interfacial phenomena within the diffusion layer of conventional electrodes.

FIGS. 5 and 5A show the disk electrode 92. The disk electrode 92 is an ultramicroelectrode having a fiber 94 and a thin film insulating layer 96 formed similar to the ultramicroelectrode 80. A ring conductor 98 made of carbon or other conductor is deposited about the insulation layer 96 by using the chemical vapor deposition process. An outer thin film layer of insulation 100 is then deposited to complete the electrode 92. The tip 95 of the electrode is exposed. At the opposite end, one lead 90 is connected to the conductor fiber 94 and a second lead 90 is connected to the conductor ring 98. At the tip end 95, the electrode 92 forms a disk as shown in FIG. 5A.

FIGS. 6 and 6A show a ring-ring disk electrode 93 with the center fiber 94 and two ring conductors 98, 99 separated by insulative layers 96, 100, 101. This construction is ideal for a fully self-contained electrochemical cell. All three conductors are combined in a single ultramicroelectrode element 93 with a total diameter for all three conductors of less than 50 micrometers. This configuration of three conductors in a single element 93 provides significant advantages in the positioning of the conductors and the readings available as compared to other ultramicroelectrode.

The major requirement for the successful chemical vapor deposition of an inorganic thin film for the fibers, wires, meshes, and foams in the present invention is that the substrate be a conductor to facilitate the resistive heating of the substrate. The thin film layers formed on top of the conductor may be insulative, semiconductive, metallic, or superconductive. A plurality of layers may be formed on the initial conductor 20 to meet specific electrode requirements.

The limiting factor in the formation of the additional layers is the thermal conductivity of the thin film layers and not the electrical conductivity. The layers are typically very thin which favors thermal conductivity. The inorganic nature of the thin films also results in excellent thermal transfer. As the substrate conductor 20 is resistively heated, the heat is transferred to the outer surface through the multiple layers to facilitate the deposition process.

In selecting the conductor substrate and inorganic layers to achieve the desired electrical effects, the elements of the precursor and the thin film resulting from the pyrolytic decomposition of the precursor vapor at the outer surface of the electrode under formation are considered. The electrical performance and bonding characteristics between layers is also considered in forming the electrode.

Figure 7:
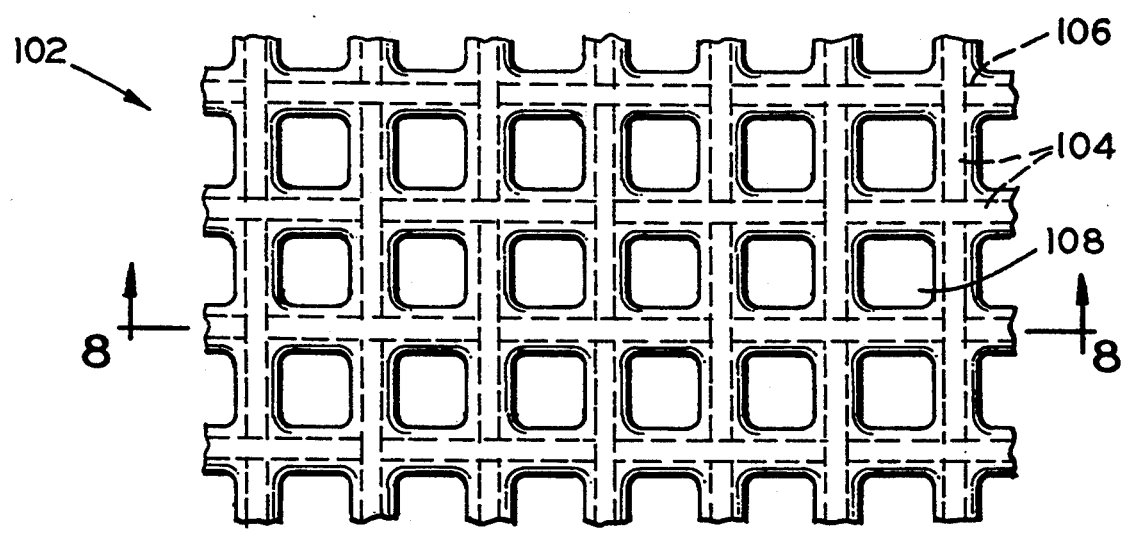
FIG. 7 is a top plan view of an electrode having a mesh conductor with a thin film layer of material deposited on the mesh.
Figure 8:
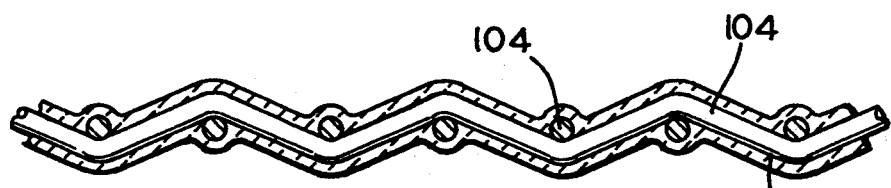
FIG. 8 is a cross sectional end view of the electrode taken along line 8—8 in FIG. 7.
Figure 9:
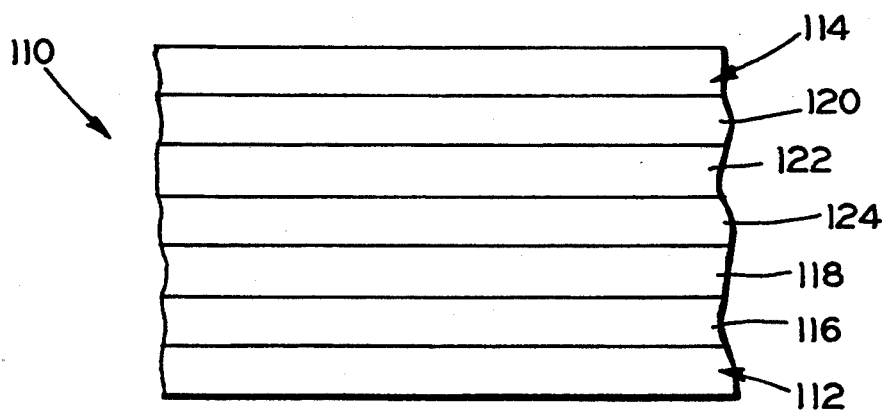
FIG. 9 is a sectional view showing a construction of a multilayered electrode having a conductor combined with additional layers of inorganic thin films.

In FIGS. 7 and 8, a mesh type layered electrode with a single thin film layer is shown. FIG. 9 displays a layered electrode with a metal foam substrate and a plurality of inorganic thin film layers. Metal foams and meshes and carbon foams provide conductive substrates which may be resistively heated for chemical vapor deposition. Applications for such electrodes include liquid chromatography detectors, and catalytic surfaces for photo reaction or electrocatalytic reaction devices.

The mesh provides a three dimensional structure and has sufficient apertures to permit optical transmission to any substrate materials. In the mesh and foam applications, semiconductor, metallic or superconductor layers are applied to a substrate to provide the desired conductivity or photosensitivity for the electrode.

FIG. 7 shows a metal mesh type conductor 102. The mesh 104 has a thin film layer 106 of a carbon film which has been deposited by chemical vapor deposition. In a solar cell application, the electrode 102 facilitates the collection of additional energy without substantially limiting the optical transparency. The apertures 108 permit light to pass through the metal mesh conductor 102.

The mesh 104 is made from gold, copper, nickel, platinum, or other similar metal. A number of different semiconductors can be used to provide the thin film coating 106, including C, Si, $CdHgTe_2$, GaAs, InSe, or $In_2Se_3$. Superconductor materials may also be deposited.

A multilayered electrode 110 is shown in FIG. 9 which may be used for an electrochromic application. In the prior art, the element 110 includes a pair of substrates 112, 114. A layer 116 of metal is deposited on substrate 112 and the inorganic electrochromic layer 118 is deposited on the metal layer 116. The other substrate 114 is formed in a similar manner having a metal layer 120 and then an inorganic electrochromic layer 122 deposited on the substrate 114. The two substrates 112, 114 are then assembled with a conducting layer 124 interposed therebetween. The element 110 in FIG. 9 can also be built using the thin film chemical vapor deposition with resistive heating of the present invention. The conductive substrate 112 is a mesh or foam substrate. The thin film layers 116, 118, 124, 122, 120, and 114 are then deposited on the substrate 112 using the simple and efficient chemical vapor deposition process. No assembly steps are required. The process of the present invention, with the thin-film coating applied by chemical vapor deposition, reduces the overall dimensions of the element 110 and provides the efficient capability of depositing a number of layers on a conductive substrate.

The foam material used for conductive substrates, such as substrate 112, is a continuous three dimensional array of interconnected conducting material oriented in a random fashion. The random structure yields a porous material with a large internal surface area for chemical vapor deposition of catalytic materials. The porous nature allows uptake of reactant materials for catalytic reactions to occur. For example, deposition of a thin film of tungsten-oxide on a conductive foam substrate gives an electrocatalyst in a flow-through configuration for the oxidation of olefins.

Figure 10:
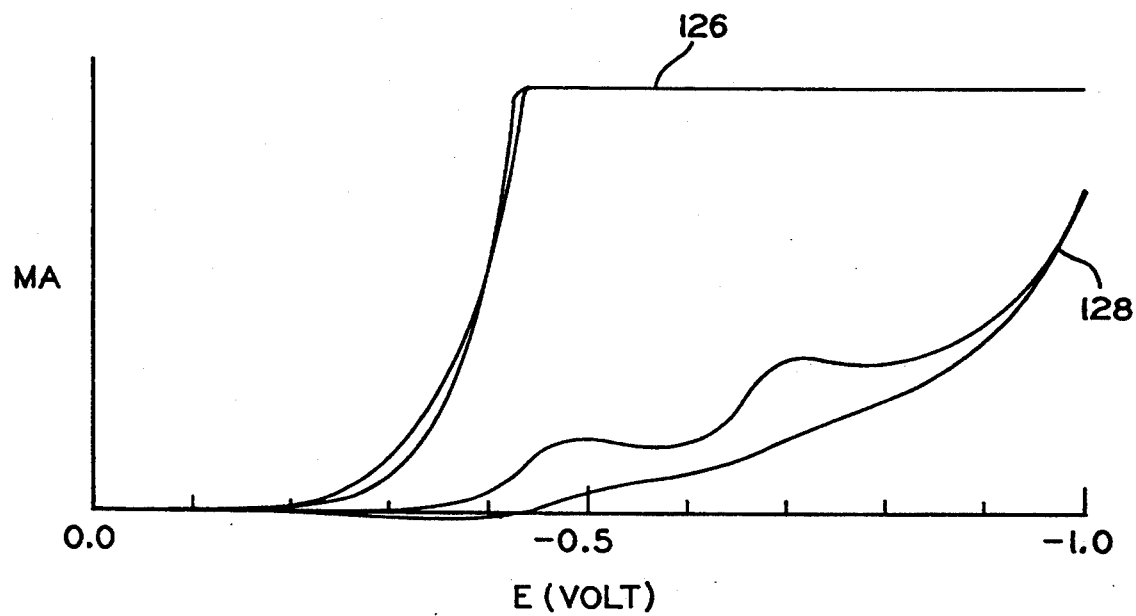
FIG. 10 is a graph showing a first cyclic voltammogram of a metallic mesh conductor without a thin film coat and a second cyclic voltammogram of a metallic mesh conductor with a carbon thin film coating.

FIG. 10 shows the benefits of the present invention in connection with the deposition of a carbon thin film on a gold micromesh. A cyclic voltammogram of 1 mM methyl viologen in 0.1M $H_2SO_4$ was taken before and after the deposition of the carbon film on the gold mesh electrode conductor. In the initial cyclic voltammogram 126, the reduction of methyl viologen is obscured by the reduction of $H^+$ to $H_2$ gas at the gold metal electrode. The result of an identical cyclic voltammogram 128 of methyl viologen at the carbon coated electrode shows the two characteristic one electron reduction waves. The hydrogen reduction has been suppressed and shifted significantly to more negative potentials.

An example of the mesh type electrode is an optically transparent electrode for spectroelectrochemical measurements. One of the improvements needed on optically transparent electrodes is to develop an electrode with a wide negative potential range. Pyrolysis of acetone on resistively heated metal mesh electrode materials provides a feasible method for the preparation of graphite coated electrodes with high optical transparencies and low electrical resistance.

When utilizing the deposition process for ultramicroelectrodes of the present invention, the reaction chamber 28 and the vaporization chamber 48 are typically maintained at atmospheric pressure. In certain circumstances, the pressure in the vaporization chamber will increase over atmospheric pressure and the pressure in the reaction chamber 28 may be reduced below atmospheric pressure to facilitate the flow of the vapor to the reaction chamber 28.

The conductor 20 is heated as noted above to a temperature of at least 100° C. The upper limit of the temperature range is limited by the decomposition or melting of the substrate, but temperatures as high as 1,400° C. have been utilized. The temperature range for the vaporization chamber 48 is in the approximate range of 30° C. to 700° C. Such temperatures facilitate the formation of a precursor vapor from a solid precursor, or from a liquid precursor and the mixing of the precursor with a blend gas in the vaporization chamber.

The quantity of precursor required depends on the size and number of conductors 20 in the process. A liquid precursor 52 could be set up on a batch basis or on an automatic flow basis. A number of inorganic precursors could be maintained and easily substituted for each other in the present deposition system. The amount of blend gas and the flow rate of the mixture from the vaporization chamber 48 to the reaction chamber is variable depending on the surface area to be covered and the desired thickness of the thin film layer.

In accordance with the provisions of the patent statutes, the present invention has been described in what is considered to represent its preferred embodiment. However, it should be noted that the invention can be practiced otherwise than as specifically illustrated and described without departing from its spirit or scope.

What is claimed is:

1. A method for making a layered electrode, said method comprising the steps of:
   a) mounting a conductor in a cold wall reaction chamber;
   b) heating said conductor through an electrical connection to a power supply;
   c) contacting a precursor vapor and a blend gas with said conductor in the reaction chamber;
   d) depositing a thin continuous film layer of an inorganic material on said conductor by pyrolytic decomposition of the precursor vapor at a surface of said conductor; and
   e) preparing the conductor with the thin-film layer for use as an electrode, including connecting a lead to the conductor.

2. The method for making a layered electrode defined in claim 1 wherein the electrode is an ultramicroelectrode having a conductor with a thickness in the range from about 0.5 micrometers to about 50.0 micrometers.

3. The method for making a layered electrode defined in claim 1 including the additional step of selecting a precursor for forming the thin film layer of inorganic material and placing the precursor in a vaporization chamber to produce the precursor vapor.

4. The method for making a layered electrode defined in claim 3 including the additional step of admitting to the vaporization chamber the blend gas in an amount to facilitate the vaporization of the precursor and to create a mixture of the precursor vapor and the blend gas having a concentration of the precursor.

5. The method for making a layered electrode defined in claim 4 including the additional step of conveying the precursor vapor and the blend gas from the vaporization chamber to the reaction chamber at a controlled rate.

6. The method for making a layered electrode defined in claim 5 including the additional step of controlling the flow of the precursor vapor and blend gas during the deposition of the thin film layer, and terminating the flow of precursor vapor and blend gas when the thin film layer has been deposited.

7. The method for making a layered electrode defined in claim 1 including the additional step of connecting said conductor to an electrical power supply and controlling a temperature of said conductor by resistive heating.

8. A method for making a layered electrode, said method comprising the steps of:
   a) selecting a conductor, and mounting said conductor in a reaction chamber;
   b) connecting said conductor to a power supply and heating said conductor by resistive heating;
   c) placing a precursor in a vaporization chamber;
   d) facilitating the vaporization of the precursor and creating a precursor vapor having a concentration of the precursor;
   e) conveying the precursor vapor from the vaporization chamber to the reaction chamber;
   f) contacting the precursor vapor with the conductor in the reaction chamber, and forming a thin continuous film coating on a surface of the conductor by a pyrolytic decomposition of the precursor vapor at the surface of the heated conductor; and
   g) controlling the concentration of the precursor, a flow rate of the precursor vapor, a temperature of the conductor, and a process time of contact in the reaction chamber until the deposition of the thin film coating on the surface of the conductor is completed.

9. The method for making a layered electrode defined in claim 8 wherein the electrode is a ultramicroelectrode having a conductor thickness between 0.5 to 50.0 micrometers, and the thin film coating is formed with a thickness on said conductor in a range from about 0.5 micrometers to about 30 micrometers.

10. The method for making an ultramicroelectrode defined in claim 9 wherein the conductor is a carbon fiber.

11. The method for making a layered electrode defined in claim 9 including the additional step of preparing the conductor with thin-film coatings for use as an ultramicroelectrode by cutting the coated conductor to a length of conductor and by connecting leads to the conductor.

12. The method for making a layered electrode defined in claim 8 wherein selecting the conductor includes selecting a conductor made from carbon.

13. The method for making a layered electrode defined in claim 12 wherein the conductor is a carbon foam.

14. The method for making a layered electrode defined in claim 8 wherein selecting the conductor includes selecting a conductor made from a metal.

15. The method for making a layered electrode defined in claim 14 wherein the conductor is a metal wire.

16. The method for making a layered electrode defined in claim 14 wherein the conductor is a metal mesh.

17. The method for making a layered electrode defined in claim 14 wherein the conductor is a metal foam.

18. The method for making a layered electrode defined in claim 8 wherein the thin-film coating is a ceramic material.

19. The method for making a layered electrode defined in claim 18 wherein the thin-film ceramic coating is selected from a member of the group consisting of carbides, nitrides, borides, oxynitrides, oxides and sulfides.

20. The method for making a layered electrode defined in claim 8 wherein the thin-film is a semiconductor material.

21. The method for making a layered electrode defined in claim 8 wherein the thin-film is a superconductor material.

22. The method for making a layered electrode defined in claim 8 wherein creating a precursor vapor includes mixing a precursor and a blend gas with oxygen such that the contacting of the precursor vapor and blend gas with the conductor takes place in the presence of oxygen.

23. The method for making a layered electrode defined in claim 22 including the additional step of scrubbing the blend gas prior to mixing the blend gas and the precursor whereby oxygen and water are removed from the blend gas and the contacting of the precursor vapor and blend gas with the conductor takes place in the absence of oxygen.

24. The method for making a layered electrode defined in claim 22 including the additional steps of monitoring a flow meter showing flow rate of the blend gas into the vaporization chamber and a flow meter showing a flow rate of the mixture of precursor vapor and blend gas into the reaction chamber, and adjusting a plurality of control valves to control such flow rates.

25. The method for making a layered electrode defined in claim 8 wherein said contacting of the precursor vapor with the conductor takes place in the reaction chamber when the temperature of the conductor is at least 100° C.

26. The method for making a layered electrode defined in claim 8 wherein creating a precursor vapor takes place in the vaporization chamber when the temperature in the vaporization chamber is in the range from about 30° C. to 700° C.

27. The method for making a layered electrode defined in claim 8 wherein said contacting of the precursor vapor with the conductor takes place in the reaction chamber when the pressure in the reaction chamber is in the range from about 0.00 atm. to about 1.00 atm.

28. The method for making a layered electrode defined in claim 8 wherein creating a precursor vapor takes place in the vaporization chamber when the pressure in the vaporization chamber is in the range from about 0.1 atm. to about 2.0 atm.

29. The method for making a layered electrode defined in claim 8 wherein the power supply connected to the conductor is a variable voltage, AC-DC power supply, and the temperature of the conductor is controlled by varying the voltage supplied to the conductor.

30. An ultramicroelectrode comprising:
 a) conductor means for collecting and conducting an electrical charge, said conductor having a thickness in the range from about 0.5 micrometers to about 50.0 micrometers; and
 b) at least one thin film layer of inorganic material formed on said conductor means, said thin film layer having a continuous and generally uniform thickness in the range of 0.5 micrometers to 30 micrometers, each of said thin film layers having at least two apertures to facilitate the collecting and conducting of the electrical charge by said conductor means;
 c) at least one lead connected to said conductor through one of the apertures in said thin film layer for conducting the electrical charge.

31. The ultramicroelectrode defined in claim 30 wherein said conductor means includes a conductor made from carbon.

32. The ultramicroelectrode defined in claim 31 wherein said conductor means is a carbon fiber.

33. The ultramicroelectrode defined in claim 32 wherein said carbon fiber is provided with a first end extending through one of the apertures in said thin film layer to form a sensor tip of the ultramicroelectrode, and a second end of said carbon fiber extending through a second aperture in said thin film layer to form a connector tip for connection to one of said leads.

34. The ultramicroelectrode defined in claim 32 including a ring conductor formed about said thin film layer of inorganic material, said ring conductor having a thickness in the range from about 0.5 micrometers to about 50.0 micrometers, and an outer ring thin film layer of inorganic material formed on said ring conductor, said thin film layer having a thickness in the range of 0.5 micrometers to 30 micrometers.

35. The ultramicroelectrode defined in claim 34 wherein said carbon fiber and said ring conductor are each provided with a first end extending through one of the apertures in said thin film layer and said outer ring thin film layer to form a disk-ring sensor tip of the ultramicroelectrode, and said carbon fiber and said ring conductor are each provided with a second end extending through a second aperture in said thin film layer and said outer ring thin film layer to form a pair of connector tips for connection to a pair of said leads.

36. The ultramicroelectrode defined in claim 34 including two additional rings formed about the second ring conductor and formed about the outer ring, a first additional ring formed of a conducting material and a second additional ring formed as an outer layer of inorganic material with each conductor connected to one of said leads to form a self-contained electrochemical cell with three leads.

37. The ultramicroelectrode defined in claim 31 wherein said conductor means is a carbon foam.

38. The ultramicroelectrode defined in claim 30 wherein said conductor means includes a conductor made from a metal.

39. The ultramicroelectrode defined in claim 38 wherein said conductor means is a metal wire.

40. The ultramicroelectrode defined in claim 38 wherein said conductor means is a metal mesh.

41. The ultramicroelectrode defined in claim 40 wherein said metal mesh includes a plurality of parallel, spaced-apart metal wires arranged in a mesh configuration, the spacing of such metal wires, with said thin film layer, forming a plurality of apertures in said mesh whereby light striking a first side of said mesh will pass through said apertures to the other side of said mesh.

42. The ultramicroelectrode defined in claim 38 wherein said conductor means is a metal foam.

43. The ultramicroelectrode defined in claim 30 wherein said thin film layer is a ceramic material.

44. The ultramicroelectrode defined in claim 43 wherein said thin film layer of ceramic material is selected from a member of the group consisting of carbides, nitrides, borides, oxynitrides, oxides and sulfides.

45. The ultramicroelectrode defined in claim 30 wherein said thin film layer is a semiconductor material.

46. The ultramicroelectrode defined in claim 30 wherein said thin film layer is a superconductor material.

47. The ultramicroelectrode defined in claim 30 wherein said thin film layer of inorganic material includes photosensitive material.

48. The ultramicroelectrode defined in claim 30 wherein said thin film layer of inorganic material is chemically inert.

* * * * *